United States Patent [19]

Preston et al.

[11] Patent Number: 5,349,072
[45] Date of Patent: Sep. 20, 1994

[54] STAGED EPOXIDATION OF PROPYLENE WITH RECYCLE

[75] Inventors: Kyle L. Preston, Port Arthur; Chung-Nan T. Wu, Houston; Mark E. Taylor, Orange; Mark A. Mueller, Austin, all of Tex.

[73] Assignee: Texaco Chemical Company, White Plains, N.Y.

[21] Appl. No.: 85,805

[22] Filed: Jul. 6, 1993

[51] Int. Cl.⁵ .................. C07D 301/19; C07D 303/04
[52] U.S. Cl. ........................................................ 549/529
[58] Field of Search ............................................. 549/529

[56] References Cited

U.S. PATENT DOCUMENTS

| | | | |
|---|---|---|---|
| 3,427,229 | 2/1969 | Herzog | 549/529 |
| 3,434,975 | 3/1969 | Sheng et al. | 549/529 |
| 3,849,451 | 11/1974 | Stein et al. | 549/529 |
| 3,928,393 | 12/1975 | Herzog | 549/529 |
| 4,626,596 | 12/1986 | Marquis et al. | 549/529 |
| 4,845,251 | 7/1989 | Marquis et al. | 549/529 |
| 4,891,437 | 1/1990 | Marquis et al. | 549/529 |
| 4,977,285 | 12/1990 | Marquis et al. | 549/529 |
| 5,107,067 | 4/1992 | Marquis et al. | 549/529 |
| 5,216,182 | 6/1993 | Marquis et al. | 549/529 |
| 5,274,138 | 12/1993 | Keating et al. | 549/529 |

Primary Examiner—Joseph E. Evans
Attorney, Agent, or Firm—James L. Bailey; Kenneth R. Priem; Carl G. Ries

[57] ABSTRACT

In reacting tertiary butyl hydroperoxide in solution in tertiary butyl alcohol with propylene to produce propylene oxide and tertiary butyl alcohol in a reactor system comprising a first isothermal segment and a second adiabatic segment about 60 to 80 wt % of the tertiary butyl hydroperoxide is converted in the isothermal segment to provide an intermediate reaction mixture, a recycle stream comprising about 25 to 100 wt. % of the combined weight of the propylene and the tertiary butyl alcohol solution is removed from the intermediate reaction mixture and recycled to the first isothermal segment and the remainder of the intermediate reaction mixture is passed through the adiabatic segment where an additional 20 to 40 wt. % of the tertiary butyl hydroperoxide is converted.

15 Claims, 3 Drawing Sheets

STAGED EPOXIDATION OF PROPYLENE WITH RECYCLE

BACKGROUND OF THE INVENTION

1. Technical Field of the Invention

This invention relates to the epoxidation of propylene. More particularly, this invention relates to a process for the reaction of propylene with tertiary butyl hydroperoxide in solution in tertiary butyl alcohol in the presence of a peroxidation catalyst to provide propylene oxide and additional tertiary butyl alcohol.

Still more particularly, this invention relates to a process for preparing propylene oxide and tertiary butyl alcohol by reacting tertiary butyl hydroperoxide in solution in tertiary butyl alcohol with propylene in the presence of a soluble molybdenum catalyst, wherein the reaction is conducted in stages involving a reactor system comprising a first isothermal segment and a second adiabatic segment, wherein a feed mixture comprising a recycle stream, propylene, and a tertiary butyl alcohol solution of tertiary butyl hydroperoxide and a molybdenum catalyst are charged to the isothermal segment under reaction conditions sufficient to provide for a conversion of about 60 to 80 wt. % of the tertiary butyl hydroperoxide to thereby provide an intermediate reaction mixture, wherein a recycle stream constituting about 25 to about 100 wt. % of the combined weight of the propylene and tertiary butyl alcohol solution is removed as the recycle stream and wherein the remainder of the intermediate reaction product is charged to the adiabatic segment for the conversion of an additional 20 to 40 wt. % of the tertiary butyl hydroperoxide to reaction products.

2. Prior Art

The reaction of an olefin such as propylene with a hydroperoxide such as tertiary butyl hydroperoxide in solution in a solvent such as tertiary butyl alcohol in the presence of a soluble molybdenum catalyst is disclosed in Kollar U.S. Pat. No. 3,351,635. Kollar teaches that in general, from about 0.5 to 100 moles of olefin may be used per mole of hydroperoxide, the preferred molar ratio being within the range of about 2 to about 10 moles of olefin per mole of hydroperoxide.

Marquis et al. in U.S. Pat. No. 4,891,437 disclose an improvement on the Kollar process in the reaction of propylene with tertiary butyl hydroperoxide is concerned wherein the reaction is conducted in a medium composed of 60 wt. % or more of polar components which is formed by utilizing a molar ratio of propylene to tertiary butyl hydroperoxide of about 0.5 to 2 moles of charged propylene per mole of charged hydroperoxide, the reaction being conducted in solution in tertiary butyl alcohol in the presence of a molybdenum catalyst. Variations in the Marquis et al. process and in the preparation of catalysts useful therefore are disclosed in Marquis et al. U.S. Pat. No. 4,845,251 and U.S. Pat. No. 5,107,067.

British Patent No. 1,298,253 discloses a process for the staged reaction of propylene with tertiary butyl hydroperoxide in the presence of tertiary butyl alcohol and a soluble molybdenum catalyst wherein the reaction product from the first stage is fractionated to provide a lighter fraction lo which is recycled to the beginning of the first stage and a heavier fraction which is charged to the second stage of the epoxidation process.

Marquis et al. U.S. Pat. No. 4,992,566 and Marquis et al. U.S. Pat. No. 5,093,506 disclose single stage processes for the reaction of propylene with tertiary butyl hydroperoxide wherein the reaction product is fractionated to provide a propylene stream for recycle.

Russell U.S. Pat. No. 3,418,340 discloses a process for the production of propylene oxide by the reaction of propylene with tertiary butyl hydroperoxide involving a recycle of the propylene wherein the propylene is further fractionated to remove oxygen prior to recycle.

Stein et al. U.S. Pat. No. 3,849,451 discloses a process wherein propylene is reacted with tertiary butyl hydroperoxide in solution in tertiary butyl alcohol in a single stage compartmented reactor operated under conditions such that propylene and propylene oxide are vaporized during the course of the reaction and wherein the vapors are recovered and distilled to provide a propylene fraction for recycle.

D'Aubigne et al. U.S. Pat. No. 4,002,687 discloses a process for the hydroperoxidation of a hydrocarbon such as isopentane or isobutane with oxygen using a plurality of stages with water washing between stages.

Background Information

Tertiary butyl hydroperoxide is a comparatively stable hydroperoxide. Nevertheless, it is a peroxide and subject to explosive autoxidation under improper conditions. The reaction of tertiary butyl hydroperoxide with propylene is a highly exothermic reaction, liberating about 60,000 calories of heat per gram mole of epoxide formed by the primary reaction. It is therefore of prime importance to maintain positive and accurate control of the reaction temperature during the epoxidation process in order to prevent a run away reaction.

It is known to achieve reaction control by conducting the reaction in a heat exchanger in indirect countercurrent contact with the heat exchange medium in order to remove excess heat of reaction as rapidly and efficiently as possible.

It is also known to moderate reaction temperature by conducting the reaction in the presence of a solvent.

Classically, both techniques have been utilized in the past in the preparation of propylene oxide from tertiary butyl hydroperoxide by conducting the reaction using a comparatively large quantity of solvent and also a large molar excess of propylene to tertiary butyl hydroperoxide, such as a molar ratio of more than 3 moles (e.g., 5 to 10 moles) of propylene per mole of tertiary butyl hydroperoxide. It is also known to conduct the reaction in a reactor provided with heat exchange control means, such as a jacket for the reactor or through the provision of internal immersed cooling coils or both.

Another problem that is encountered in the reaction of propylene with tertiary butyl hydroperoxide relates to selectivity. Although the primary reaction of the tertiary butyl hydroperoxide with propylene will result in the formation of propylene oxide and tertiary butyl alcohol, other oxygenated by-products can be and are formed in various amounts, including aldehydes, organic acids, esters, ketones, etc. Moreover, the propylene oxide that is formed can react with oxygenated by-products present in the reaction medium to further decrease the yield of propylene oxide.

Another problem as pointed out in Marquis et al. U.S. Pat. No. 4,891,437, is the tendency of propylene to react with itself under epoxidation conditions to form an addition product containing 6 or more carbon atoms. These hydrocarbon by-products are particularly pernicious in that they tend to codistill with and to be present in the final propylene oxide product where they significantly and adversely affect its quality. This problem can be minimized by use of a comparatively low mole ratio of propylene to tertiary butyl hydroperoxide, such as a molar ratio of about 1 to about 2 moles of propylene per mole of tertiary butyl hydroperoxide.

SUMMARY OF THE INVENTION

In accordance with the present invention, the foregoing and other problems are ameliorated through the provision of a process wherein propylene is reacted with tertiary butyl hydroperoxide in a staged process in a reactor system comprising a first isothermal segment and a second adiabatic segment, wherein the isothermal segment is charged with propylene, with a tertiary butyl alcohol solution of tertiary butyl hydroperoxide and molybdenum catalyst and a recycle stream, wherein the reaction conditions in the isothermal segment are established so as to convert about 60 to about 80 wt. % of the tertiary butyl hydroperoxide to an intermediate reaction mixture, wherein a portion of the intermediate reaction mixture, constituting about 25 to about 100 wt. % of the combined weight of the initial propylene and tertiary butyl alcohol solution, is removed from the intermediate reaction mixture as the recycle stream, wherein the remainder of the intermediate reaction stream is charged to the adiabatic segment of the reactor system in order to convert an additional 20 to 40 wt. % of the tertiary butyl hydroperoxide to propylene oxide and other products. Propylene oxide and tertiary butyl alcohol are the principal reaction products and can be recovered by distillation. Any excess propylene can also be recovered for recycle as part of the initial propylene charge strew.

In accordance with the preferred embodiment of the present invention, the process is carried out continuously in a reaction zone comprising a first isothermal segment and a second adiabatic segment, and wherein:

a) a tertiary butyl alcohol solution is prepared containing about 35 to about 60 wt. % of tertiary butyl hydroperoxide, correspondingly about 65 to about 40 wt. % of tertiary butyl alcohol, and about 100 to about 1,000 ppm of a soluble molybdenum catalyst, b) there is continuously charged to the isothermal segment a feed mixture comprising propylene, the tertiary butyl alcohol solution, and also a recycle stream comprising about 25 to about 100 wt. % of the combined weight of the propylene and the tertiary butyl alcohol solution, the propylene being charged in an amount sufficient to provide an initial charge ratio of about 1 to about 3 moles of propylene per mole of tertiary butyl hydroperoxide, c) the feed mixtures continuously passed through the isothermal segment under epoxidation reaction conditions of time and temperature sufficient to convert about 60 to about 80% of the tertiary butyl hydroperoxide to reaction products including propylene oxide, tertiary butyl alcohol and oxygenated by-products and to provide an isothermal segment reaction product, d) continuously removing the said recycle stream from the isothermal segment reaction product to provide an intermediate reaction mixture comprising the remainder of the isothermal segment reaction product, e) continuously returning the recycle stream to the isothermal segment, f) continually charging the remainder of the intermediate reaction mixture to the adiabatic segment and flowing it therethrough under adiabatic epoxidation reaction conditions of temperature and time sufficient to convert an additional 20 to 40% of the charged tertiary butyl hydroperoxide to reaction products including propylene oxide, tertiary butyl alcohol and oxygenated by-products, g) continually recovering propylene oxide and tertiary butyl alcohol from the final product.

The epoxidation reaction conditions utilized in the isothermal epoxidation segment may suitably include a temperature of about 50° to about 180° C. and a reaction time of about 0.3 to about 3 hours. More preferably, the reaction will be conducted at a pressure of about 400 to about 800 psig, a reaction temperature of about 80° to about 140° C. and a reaction time of about 0.5 to about 2 hours.

Reaction conditions are preferably adjusted in the isothermal segment to provide for about a 65 to about a 75% conversion of the tertiary butyl hydroperoxide and for the recycle of a recycle stream comprising about 25 to about 100 wt. % of the combined weight of the propylene charge stream and the tertiary butyl alcohol solution.

A problem involved in the recycle of the total reactor effluent from the isothermal segment arises in that the recycle stream is at a temperature of 100° to 140° C. and contains tertiary butyl hydroperoxide and possibly other hydroperoxide reaction products which may be less thermally stable than the tertiary butyl hydroperoxide. Therefore, when a pump is utilized to provide the motive force for recycling the recycle stream, care must be taken to avoid a potential source of ignition, such as a spark generated by the equipment. Failure of a mechanical pump can also lead to a runaway reaction, especially if olefin impurities such as butylenes and/or pentalenes are present. A mechanical pump may provide an ignition source in the event of the failure of a bearing, a rotor or some other part which permits the creation of a local hot spot. Also, it is not uncommon for a mechanical pump to experience deterioration of the seals which can lead to the release of environmentally noxious or hazardous materials.

In accordance with a modified form the present invention, these and other problems are ameliorated through the provision of a jet pump or eductor in order to provide the motive force for transporting the recycle stream from the effluent end of the adiabatic segment to the charge end.

DESCRIPTION OF THE PREFERRED EMBODIMENT

Figure 1:
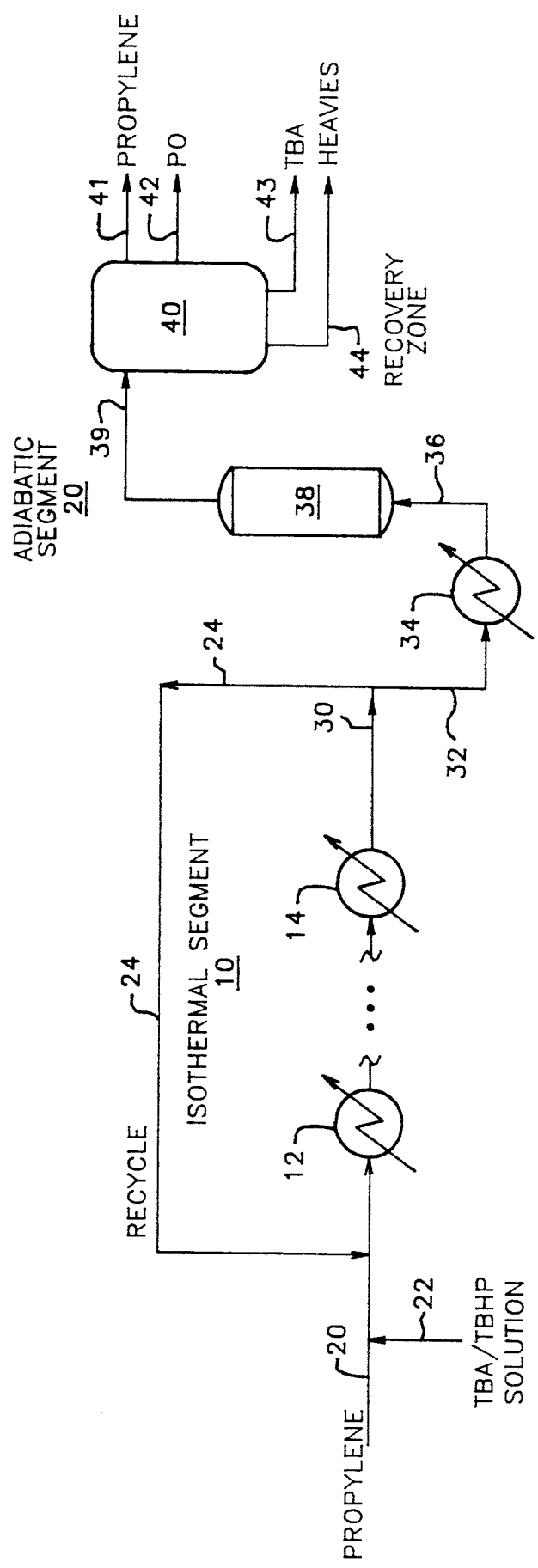
FIG. 1 is a schematic flow sheet illustrating the general reaction sequence of the present invention.

Turning now to the drawings, and in particular to FIG. 1, there is shown a schematic flow sheet illustrating a preferred method of practicing the process of the present invention. In the drawing, conventional parts, such as valves, pumps, temperature sensors, pressure sensors, heaters, coolers, flow control regulation apparatus, etc., have been omitted.

In accordance with this embodiment of the present invention, there is provided a reactor system comprising an isothermal segment designated generally by the numeral 10 and an adiabatic segment designated generally by the numeral 20.

The isothermal segment 10 will comprise a plurality of reactors 12–14, each provided with appropriate indirect heat exchange control means.

In order to initiate the process, propylene is charged to the initial reactor 12 by way of a charge line 20 together with a tertiary butyl alcohol solution of tertiary butyl hydroperoxide containing a molybdenum catalyst which is charged by a line 22 and with a recycle stream 24. The resultant reaction mixture is passed through the series of reactors 12–14 in the isothermal segment under conditions of temperature, pressure and time sufficient to convert from about 60 to about 80 wt. % of the charged tertiary butyl hydroperoxide. The reaction conditions to be utilized in the isothermal segment may include a pressure sufficient to maintain the reactants in liquid phase, such as a pressure of about 400 to about 800 psig, a reaction temperature of about 50° to about 180° C., such as a temperature of about 100° to about 130° C., and a reaction time of about 0.3 to about 3 hours, and more preferably from about 0.5 to about 2 hours. The reactor effluent from the last of the isothermal reactors 14 is discharged by a line 30 which is provided with a branch line 24 from which the recycle stream is removed and with a second line 32 leading to an appropriate heat exchange means 34 for adjusting the temperature, if necessary, of the resultant remainder of the intermediate reaction mixture after which it is charged by a line 36 to an adiabatic reactor 38 in the adiabatic reaction segment 20 to convert an additional 15 to 20 wt. % of the tertiary butyl hydroperoxide therein.

The products of the reaction are discharged in the adiabatic reaction segment 38 by a line 39 leading to a recovery zone 40 wherein the products of the reaction may be separated by conventional distillation means, such as those described in Marquis et al. U.S. Pat. No. 4,992,556 or Marquis et al. U.S. Pat. No. 5,093,506. For example, the recovery zone 40 may comprise a plurality of serially connected distillation columns wherein the products of the reaction are separated into a propylene fraction 41 that can be recycled by any suitable means (not shown) as part of the propylene charge 20, a propylene oxide fraction 42, a tertiary butyl alcohol fraction 43 comprising charged tertiary butyl alcohol and tertiary butyl alcohol formed during the process, and a heavier fraction 44 comprising reaction byproducts and catalyst residue.

By way of example, about 1000 pounds per hour of propylene may be charged to the isothermal segment by the line 20 together with about 2430 pounds per hour of a solution of tertiary butyl hydroperoxide in tertiary butyl alcohol which is charged by the line 22. Suitably, the solution will contain about 55 wt. % of tertiary butyl hydroperoxide. A recycle stream charged by the line 24 may comprise, for example, about 370 pounds per hour of propylene, about 360 pounds per hour of propylene oxide, about 1120 pounds per hour of tertiary butyl alcohol and about 240 pounds per hour of tertiary butyl hydroperoxide.

The feed mixture is passed through the isothermal reactor segment reactors 12–14 under reaction conditions including a temperature of about 80° to about 140° C. a pressure of about 400 to about 800 psig and a total reaction time within the isothermal segment of about 0.3 to about 2 hours.

The effluent of about 5490 pounds per hour discharged by the line 30 is separated into 2060 pounds per hour of recycle and about 3430 pounds per hour of feed to the adiabatic reaction segment 38 by way of the lines 32 and 36.

Figure 2:
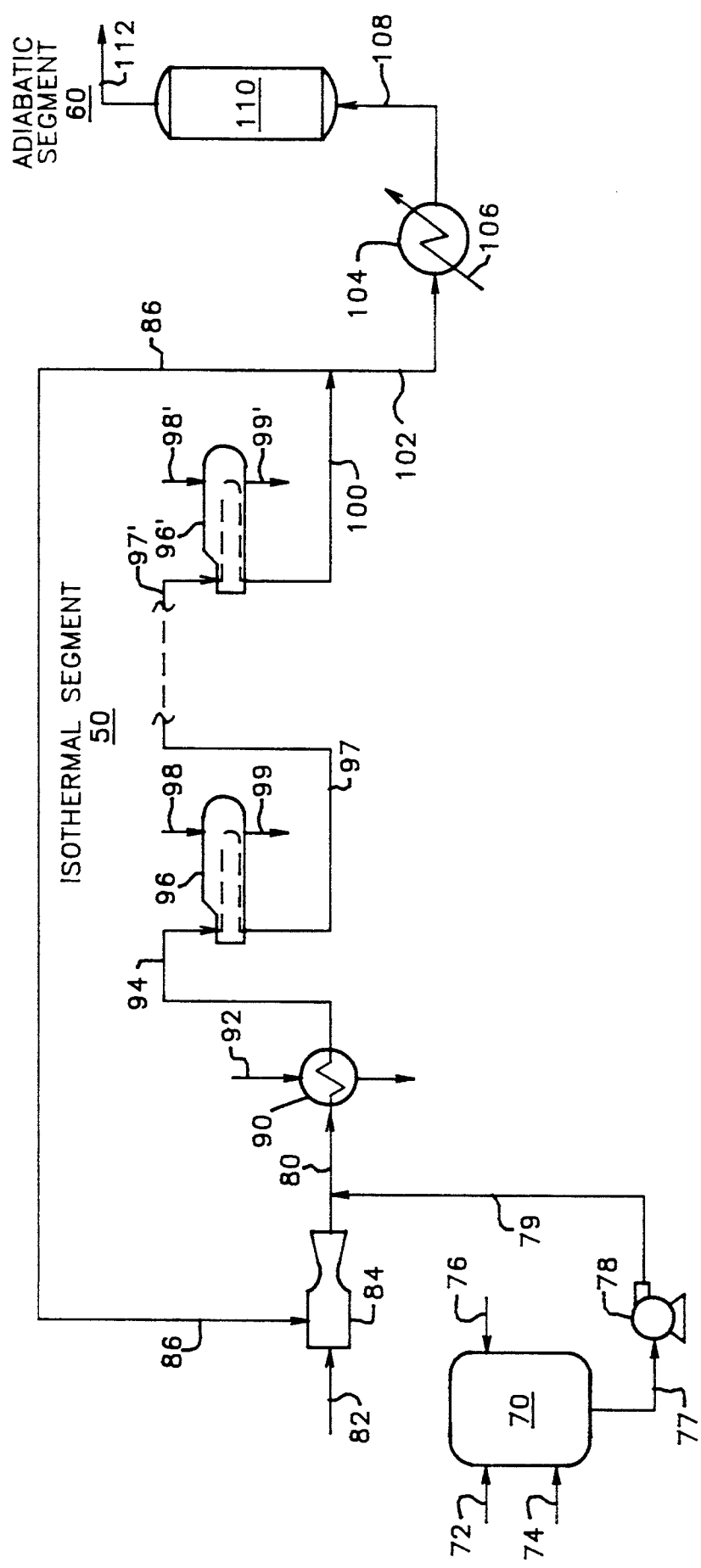
FIG. 2 is a schematic flow sheet illustrating the embodiment of the present invention wherein an eductor is utilized to transport the recycle stream.

Turning now to FIG. 2, there is shown a preferred embodiment of the present invention wherein an eductor is utilized to transport the recycle stream from the isothermal reactor effluent to the beginning of the process.

Turning now to FIG. 2, there is shown a reaction system comprising an isothermal reactor segment 50 and an adiabatic reactor segment 60.

There is also provided a feedstock preparation tank designated generally by the number 70 to which tertiary butyl hydroperoxide is charged by a line 72 and where it is maintained at a temperature of not more than about 60° C. A catalyst solution, such as a molybdenum/ethylene glycol complex in solution in ethylene glycol is also charged to the preparation tank 70 by a line 74, the reactants being suitably charged in proportions such that the feed in the tank 70 contains about 35 to about 60 wt. % of tertiary butyl hydroperoxide, correspondingly about 65 to about 40 wt. % of tertiary butyl alcohol and about 100 to about 1,000 ppm of the molybdenum catalyst solution. The feed mixture may be discharged from the feed tank 70 by a discharge line 77 leading to a pump 78 of any conventional construction for charging the tertiary butyl alcohol solution by a feed line 79 to a charge line 80 leading to the isothermal segment 50. Propylene is charged to the process by a propylene charge line 82 passing through an eductor 84 of any conventional construction wherein the eductor orifice size, differential pressure and flow rate of the propylene are adjusted so as to educt a desired Mount of a recycle stream into the eductor by way of a line 86. Suitably, the quantity of material educted into the line 86 will constitute from about 25 to about 100 wt. % of the combined weight of the propylene feed in the line 82 and the tertiary butyl alcohol feed in the line 79 and, still more preferably, from about 50 to about 80 wt. %.

Line 80 may suitably lead to a preheater 90 of any conventional construction wherein the feed mixture is brought to a desired reaction temperature by a heat exchange medium passed through the heat exchange preheater 90 by way of a line 92. The heated material is then passed by a line 94 to a first isothermal reactor 96 which may, for example, be a jacketed reactor wherein the reactants are immersed in a heat exchange fluid such as water which is passed through the reactor 96 by way of a heat exchange charge line 98 which discharges from the reactor by a heat exchange discharge line 99. By adjusting the temperature or flow of the heat exchange medium 92, the flow rates of lines 82 and the line 79, appropriate reaction conditions can be established in the isothermal segment including a pressure sufficient to maintain the reactants in liquid phase, such as a pressure of about 400 to about 800 psig, a reaction temperature of about 50° to about 180° C., and more preferably from about 80° to about 140° C., and a reaction time of about 0.3 to about 3 hours, such as a reaction time of about 0.5 to about 2 hours. The isothermal segment will comprise a plurality of the heat exchange reactors 96, the last reactor in the series being a reactor 96' through which a heat exchange medium is passed by way of heat exchange charge line 98' and discharged by way of heat exchange discharge line 99', the reactor effluent from the first of the isothermal segment reactors 96 is discharged by a line 97 leading to the next succeeding reactor and hence in sequence until the final charge mixture is charged by a line 97' to the heat exchange reactor 96'. The final reactor effluent is discharged from the reactor 96' by a line 100 provided with a branch line 86 from which the desired quantity of reactor effluent is educted for recycle through the eductor 84. Suitably, the amount of educted material will constitute about 25 to about 100 wt. % of the combined weight of the propylene and tertiary butyl alcohol solution and, more preferably, from about 50 to about 80 wt. %. The remainder of the intermediate reaction mixture discharged by the line 100 will be charged by way of a line 102 leading to a heat exchanger 104 provided with an indirect heat exchange means such as a flow line 106 for adjusting the temperature of the intermediate reaction mixture, after which it is charged by way of a line 108 to the adiabatic segment reactor 110 where an additional 20 to 40% of the tertiary butyl hydroperoxide is converted. Thereafter, the reactor effluent is discharged from the adiabatic segment 100 by a line 112 leading to a distillation zone (not shown) wherein the reaction effluent may be fractionated into suitable fractions such as a propylene fraction which can be recycled by suitable means (not shown) as part of the propylene charge 82, a propylene oxide product fraction, a tertiary butyl alcohol fraction comprising charged tertiary butyl alcohol and tertiary butyl alcohol formed during the process, and a heavier fraction comprising the reaction by-products and catalyst residue.

Figure 3:
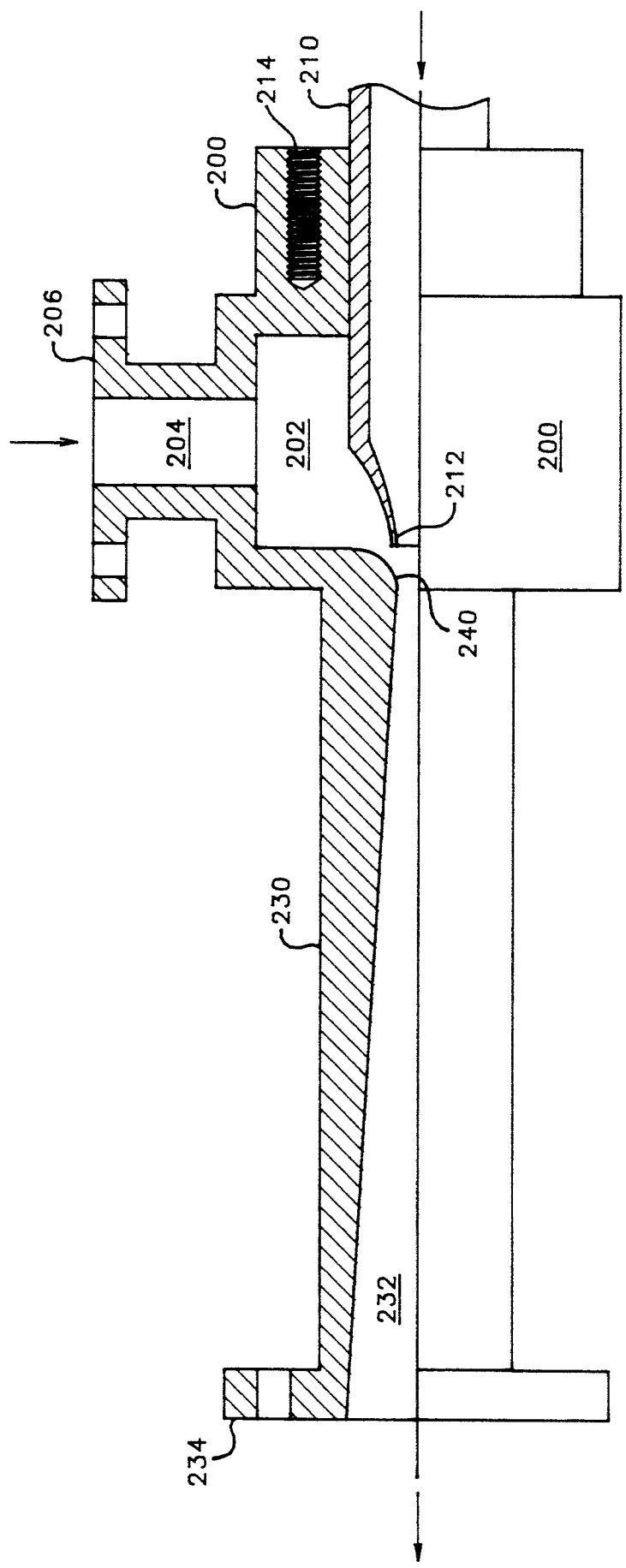
FIG. 3 is a plan view, partially in section, of an eductor of the type that may be used in the process of the present invention.

Turning now to FIG. 3, there is shown the design of an eductor of the type that can be used in the process of the present invention.

It will be understood that the eductor shown in FIG. 3 is given by way of example and that eductors of a different design are commercially available and can be used in the process of the present invention such as a Fisher spike nozzle model 12TC or a Fisher standard model 12TC.

As shown in FIG. 3, the eductor or jet pump comprises a housing 200 defining a chamber 202 having an inlet opening 204 through which liquid may be educted into the chamber 202. A flange or any other suitable means 206 is provided for securing an inlet pipe to the opening 204. A charge line 210 is provided entering from the rear of the housing 200 and terminating inside the chamber 202 in an eduction nozzle segment 212.

Suitable means such as a tap 214 is provided for securing the housing 200 to a support mechanism through which the charge line 210 may be passed.

The eductor 200 is also provided with a discharge barrel 230 having an outwardly flaring discharge channel 232 into which the charged liquid from the charge line 210 and the liquid from the chamber 202 are mixed and discharged. Suitable fastening means such as a flange 234 may be provided for securing the barrel to a discharge pipe (not shown).

By adjusting the discharge angle, the sides of the throat 240 at the entrance of the barrel, the shape of the nozzle 212 and the tolerance between the two, it is possible to provide for a motive force sufficient to move a desired quantity of liquid from a suitable source (not shown) through the inlet line 204 to the chamber 202 and thence in admixture with charge liquid from charge line 210 into the barrel 232 for discharge from the system.

Having thus described our invention, what is claimed is:

1. In a process for preparing propylene oxide and tertiary butyl alcohol by reacting propylene with tertiary butyl hydroperoxide in solution in tertiary butyl alcohol in the presence of a soluble peroxidation catalyst, the improvement which comprises:
   conducting said process in a reactor system comprising a first isothermal segment and a second adiabatic segment,
   charging to said isothermal segment a feed mixture comprising a recycle stream, propylene and a tertiary butyl alcohol solution of tertiary butyl hydroperoxide and molybdenum catalyst,
   converting about 50 to 80 wt. % of the tertiary butyl hydroperoxide in the isothermal segment to provide an intermediate reaction mixture,
   removing a recycle stream from the intermediate reaction mixture and recycling it to the first isothermal segment as said recycle stream, and
   passing the remainder of the intermediate reaction mixture through the adiabatic segment and converting therein an additional 20 to 40 wt. % of the tertiary butyl hydroperoxide charged thereto,
   said recycle stream being about 25 to about 100 wt. % of the initial feed mixture.

2. In a process for preparing propylene oxide and tertiary butyl alcohol by reacting propylene with tertiary butyl hydroperoxide in solution in tertiary butyl alcohol in the presence of a soluble molybdenum catalyst, the improvement which comprises:
   continuously conducting said process in a reactor system comprising a first isothermal segment and a second adiabatic segment,
   preparing a tertiary butyl alcohol solution containing about 35 to about 60 wt. % of tertiary butyl hydroperoxide, correspondingly, about 65 to about 40 wt. % of tertiary butyl alcohol and about 100 to about 1,000 ppm of a soluble molybdenum catalyst,
   continuously educting a recycle stream into a flowing stream of propylene in an eductor, said recycle stream being about 25 to about 100 wt. %, of the combined weight of the propylene, and of the tertiary butyl alcohol solution,
   continuously charging to said isothermal segment a feed mixture comprising said educted recycle stream, said propylene and said tertiary butyl alcohol solution, and converting about 60 to 80 wt. % of the charged tertiary butyl hydroperoxide therein to provide an intermediate reaction mixture,
   removing said recycle stream from the intermediate reaction mixture, and
   passing the remainder of the intermediate reaction mixture through the adiabatic segment and converting therein an additional 20 to 40 wt. % of the tertiary butyl hydroperoxide charged thereto.

3. In a process for the preparation of tertiary butyl alcohol and propylene oxide by reacting propylene with tertiary butyl hydroperoxide in the presence of a molybdenum catalyst at an elevated temperature and a pressure sufficient to maintain the reactants in liquid phase, said reaction being conducted in a reaction zone comprising a first isothermal segment and at a second adiabatic segment, the improvement which comprises the steps of:
   a. preparing a tertiary butyl alcohol solution containing about 35 to about 60 wt. % of tertiary butyl hydroperoxide, correspondingly, about 65 to about 40 wt. % of tertiary butyl alcohol and about 100 to about 1,000 ppm of a soluble molybdenum catalyst, b. continuously charging to said isothermal segment a feed mixture comprising propylene, said tertiary butyl alcohol solution and a recycle stream comprising about 25 to 100 wt. % of the combined weight of said propylene and said tertiary butyl alcohol solution, said propylene being charged in an amount sufficient to provide an initial charge ratio of about 1 to about 3 moles of propylene per mole of tertiary butyl hydroperoxide, c. continuously passing said feed mixture through said isothermal segment under epoxidation reaction conditions of time and temperature sufficient to convert about 60 to about 80% of the tertiary butyl hydroperoxide to reaction products including propylene oxide and tertiary butyl alcohol, and to provide an isothermal segment reaction product, d. continuously removing said recycle stream from said isothermal segment reaction product to provide an intermediate reaction mixture comprising the remainder of said isothermal segment reaction product, e. continuously returning said recycle stream to said isothermal segment, f. continuously charging said intermediate reaction mixture to said adiabatic segment and flowing said intermediate reaction mixture therethrough under adiabatic epoxidation reaction conditions of temperature and time sufficient to convert therein an additional 20 to 40 wt. % of the tertiary butyl hydroperoxide charged thereto to reaction products, principally propylene oxide and tertiary butyl alcohol to provide a final reaction product, and g. continuously recovering propylene oxide and tertiary butyl alcohol from said final reaction product, h. said epoxidation reaction conditions in said isothermal segment and said adiabatic segment of said epoxidation reaction zone including a temperature of about 50° to 180° C., and a reaction time of about 0.3 to about 3 hours.

4. A process as in claim 3 wherein the epoxidation reaction conditions include a temperature of about 100° to about 130° C., a pressure of about 400 to about 800 psig and a reaction time of about 0.5 to about 2 hours.

5. A process as in claim 4 wherein the epoxidation reaction conditions include a temperature of about 110 to about 140° C., a pressure of about 500 to about 700 psig and a reaction time of about 0.5 to about 2 hours in the isothermal segment and a temperature of about 110 to about 140° C., a pressure of about 500 to about 700 psig and a reaction time of about 0.5 to about 2 hours in the adiabatic segment.

6. A process as in claim 5 wherein the reaction conditions are adjusted in the isothermal segment to provide for about a 65 to about a 75% conversion of the tertiary butyl hydroperoxide and wherein the recycle stream comprises about 40 to 80 wt. % of the combined weight of the charged propylene and tertiary butyl alcohol solution.

7. In a process for the preparation of tertiary butyl alcohol and propylene oxide by reacting propylene with tertiary butyl hydroperoxide in the presence of a molybdenum catalyst at an elevated temperature and at a pressure sufficient to maintain the reactants in liquid phase, said reaction being conducted in a reaction zone comprising a first isothermal segment and at a second adiabatic segment, the improvement which comprises the steps of:

a. preparing a tertiary butyl alcohol solution containing about 35 to about 60 wt. % of tertiary butyl hydroperoxide, correspondingly, about 65 to about 40 wt. % of tertiary butyl alcohol and about 100 to about 1,000 ppm of a soluble molybdenum catalyst, b. continuously educting a recycle stream into a stream of propylene, said recycle stream comprising about 25 to about 100 wt. % of the combined weight of said propylene, and tertiary butyl alcohol solution, c. continuously charging to said isothermal segment a feed mixture comprising said recycle stream, and propylene and said tertiary butyl alcohol solution, said propylene being charged in an amount sufficient to provide an initial charge reaction mixture having a charge ratio of about 1 to about 3 moles of propylene per mole of tertiary butyl hydroperoxide, d. condinuously passing said initial charge reaction mixture through said isothermal segment under reaction conditions of time and temperature sufficient to convert about 60% to about 80% of the tertiary butyl hydroperoxide to reaction products including propylene oxide and tertiary butyl alcohol, and to provide an isothermal segment reaction product, e. continuously removing said recycle stream from said isothermal segment reaction product to provide an intermediate reaction mixture comprising the remainder of said isothermal segment reaction product, f. continuously charging said intermediate reaction mixture to said adiabatic segment and flowing said intermediate reaction mixture therethrough under adiabatic reaction conditions of temperature and pressure sufficient to convert therein an additional 20 to 40 wt. % of the tertiary butyl hydroperoxide charged thereto to reaction products, principally propylene oxide and tertiary butyl alcohol to provide a final reaction product, and g. continuously recovering propylene oxide and tertiary butyl alcohol from said final reaction product, h. said epoxidation reaction conditions in said isothermal segment and said adiabatic segment of said epoxidation reaction zone including a temperature of about 50° to 180° C., a pressure sufficient to maintain the reactants and the reaction products in liquid phase and a reaction time of about 0.3 to about 5 hours.

8. A process as in claim 7 wherein the epoxidation reaction conditions include a temperature of about 100° to about 130° C., a pressure of about 400 to about 800 psig and a reaction time of about 0.5 to about 2 hours.

9. A process as in claim 7 wherein the epoxidation reaction conditions include a temperature of about 80° to about 140° C., a pressure of about 400 to about 800 psig and a reaction time of about 0.5 to about 2 hours in the isothermal segment and a temperature of about 110 to about 140° C., a pressure of about 500 to about 800 psig and a reaction time of about 0.5 to about 2 hours in the adiabatic segment.

10. In a continuous process for preparing propylene oxide and tertiary butyl alcohol wherein propylene and tertiary butyl hydroperoxide are reacted in an epoxidation reaction zone under predetermined reaction conditions, said epoxidation reaction zone comprising an isothermal segment and an adiabatic segment, said propylene being reacted with said tertiary butyl hydroperoxide in solution in tertiary butyl alcohol in the presence of a catalytic amount of a soluble complex of molybdenum with ethylene glycol the improvement which comprises the steps of:

a. preparing a tertiary butyl alcohol solution containing about 35 to about 60 wt. % of tertiary butyl hydroperoxide, correspondingly, about 65 to about 40 wt. % of tertiary butyl alcohol and about 100 to about 1,000 ppm of a soluble molybdenum catalyst, b. continuously educting a recycle stream into a propylene stream, said recycle stream comprising at 25 to about 100 wt. % of the combined weight of the propylene and the tertiary butyl alcohol solution, c. charging to said isothermal segment a feed mixture comprising said recycle stream, and propylene stream and said tertiary butyl alcohol solution, said propylene being charged in an amount sufficient to provide an initial charge ratio of about 1 to about 3 moles of propylene per mole of tertiary butyl hydroperoxide, d. continuously passing said feed mixture through said isothermal segment under reaction conditions of time and temperature sufficient to convert about 60% to about 80% of the tertiary butyl hydroperoxide to reaction products including propylene oxide and tertiary butyl alcohol, and to provide an isothermal segment reaction product, e. continuously removing said recycle stream from said isothermal segment reaction product to provide an intermediate reaction mixture comprising the remainder of said isothermal segment reaction product, f. continuously charging said intermediate reaction mixture to said adiabatic segment and flowing said intermediate reaction mixture therethrough under adiabatic reaction conditions of temperature and pressure sufficient to convert therein an additional 20 to 40 wt. % of the tertiary butyl hydroperoxide charged thereto to reaction products to provide a final epoxidation reaction product comprising unreacted propylene, unreacted tertiary butyl hydroperoxide, propylene oxide, tertiary butyl alcohol, dissolved molybdenum-ethylene glycol catalyst complex, and oxygen-containing impurities, and g. continuously charging said final epoxidation reaction product to a distillation zone and resolving it therein into distillation fractions, including a distillate propylene fraction, a distillate propylene oxide fraction, a distillate tertiary butyl alcohol fraction and a bottoms fraction composed primarily of tertiary butyl hydroperoxide, tertiary butyl alcohol, oxygen-containing impurities and dissolved molybdenum-ethylene glycol catalyst complex, h. said epoxidation reaction conditions in said isothermal segment and said adiabatic segment of said epoxidation reaction zone including a temperature of about 50° to 180° C., a pressure sufficient to maintain the reactants and the reaction products in liquid phase and a reaction time of about 0.3 to about 5 hours.

11. A process as in claim 10 wherein the epoxidation reaction conditions include a temperature of about 80° to about 130° C., a pressure of about 400 to about 800 psig and a reaction time of about 0.5 to about 4 hours.

12. A process as in claim 10 wherein the epoxidation reaction conditions include a temperature of about 80° to about 140° C., a pressure of about 500 to about 800 psig and a reaction time of about 0.5 to about 2 hours in the isothermal segment and a temperature of about 110 to about 140° C., a pressure of about 500 to about 800 psig and a reaction time of about 0.5 to about 2 hours in the adiabatic segment.

13. In a continuous process for preparing propylene oxide and tertiary butyl alcohol wherein propylene and tertiary butyl hydroperoxide are reacted in an epoxidation reaction zone under predetermined reaction conditions, said epoxidation reaction zone comprising an isothermal segment and an adiabatic segment, said propylene being reacted with said tertiary butyl hydroperoxide in solution in tertiary butyl alcohol in the presence of a catalytic amount of a soluble complex of molybdenum with ethylene glycol the improvement which comprises the steps of:

a. preparing a tertiary butyl alcohol solution containing about 35 to about 60 wt. % of tertiary butyl hydroperoxide, correspondingly, about 65 to about 40 wt. % of tertiary butyl alcohol and about 100 to about 1,000 ppm of a soluble molybdenum catalyst, b. continuously educting a recycle stream into a propylene stream in said eductor, said recycle stream comprising about 25 to about 100 wt. % of the combined weight of the propylene and the tertiary butyl alcohol solution, c. charging a feed mixture to said isothermal segment in admixture, said feed mixture comprising said recycle stream, said propylene stream and said tertiary butyl alcohol solution, said propylene being charged in an amount sufficient to provide an initial charge reaction mixture having a ratio of about 1 to about 3 moles of propylene per mole of tertiary butyl hydroperoxide, d. continuously passing said feed mixture through said isothermal segment under reaction conditions of time and temperature sufficient to convert about 60% to about 80% of the tertiary butyl hydroperoxide and to provide an isothermal segment reaction product, e. continuously charging said intermediate reaction mixture to said adiabatic segment and flowing said intermediate reaction mixture therethrough under adiabatic reaction conditions of temperature and pressure sufficient to convert therein an additional 20 to 40 wt. % of the tertiary butyl hydroperoxide charged thereto to reaction products to provide a final epoxidation reaction product comprising unreacted propylene, unreacted tertiary butyl hydroperoxide, propylene oxide, tertiary butyl alcohol, dissolved molybdenum-ethylene glycol catalyst complex, and oxygen-containing impurities, and f. continuously charging said final epoxidation reaction product to a distillation zone and resolving it therein into distillation fractions, including a distillate propylene fraction, a distillate propylene oxide fraction, a distillate tertiary butyl alcohol fraction and a bottoms fraction composed primarily of tertiary butyl hydroperoxide, tertiary butyl alcohol, oxygen-containing impurities and dissolved molybdenum-ethylene glycol catalyst complex, g. said epoxidation reaction conditions in said isothermal segment and said adiabatic segment of said epoxidation reaction zone including a temperature of about 50° to 180° C., a pressure sufficient to maintain the reactants and the reaction products in liquid phase and a reaction time of about 0.3 to about 5 hours.

14. A process as in claim 13 wherein the epoxidation reaction conditions include a temperature of about 100° to about 130° C., a pressure of about 400 to about 800 psig and a reaction time of about 0.5 to about 4 hours.

15. A process as in claim 13 wherein the epoxidation reaction conditions include a temperature of about 80° to about 140° C., a pressure of about 500 to about 800 psig and a reaction time of about 0.5 to about 2 hours in the isothermal segment and a temperature of about 110 to about 140° C., a pressure of about 500 to about 800 psig and a reaction time of about 0.5 to about 2 hours in the adiabatic segment.

* * * * *

UNITED STATES PATENT AND TRADEMARK OFFICE
CERTIFICATE OF CORRECTION

PATENT NO. : 5,349,072
DATED : September 20, 1994
INVENTOR(S) : Kyle Lee Preston et al.

It is certified that error appears in the above-indentified patent and that said Letters Patent is hereby corrected as shown below:

Column 10:
In Claim 7, line 7, please delete "about".
Column 10:
In Claim 7, line 21, please substitute --continuously--
for "condinuously".
Column 11:
In Claim 10, line 17, please substitute --said-- for "and".
Column 12:
In Claim 13, line 33, after "a" insert --charge--.

Signed and Sealed this

Thirteenth Day of December, 1994

Attest:

BRUCE LEHMAN

*Attesting Officer*      *Commissioner of Patents and Trademarks*